United States Patent [19]

Stevens et al.

[11] Patent Number: 5,064,802

[45] Date of Patent: Nov. 12, 1991

[54] METAL COMPLEX COMPOUNDS

[75] Inventors: James C. Stevens, Midland, Mich.; David R. Neithamer, Concord, Calif.

[73] Assignee: The Dow Chemical Company, Midland, Mich.

[21] Appl. No.: 547,728

[22] Filed: Jul. 3, 1990

Related U.S. Application Data

[63] Continuation-in-part of Ser. No. 407,169, Sep. 14, 1989, abandoned.

[51] Int. Cl.$^5$ .............................. C08F 4/64; C08F 4/68; C08F 4/69; C08F 4/62
[52] U.S. Cl. .................................. 502/155; 502/102; 502/103; 502/104; 502/117; 502/152; 526/134; 526/170; 556/7; 556/8; 556/10; 556/11; 556/19; 556/52
[58] Field of Search ............... 502/102, 103, 104, 117, 502/152, 155; 556/7, 8, 10, 11, 19, 52

[56] References Cited

FOREIGN PATENT DOCUMENTS

| 277003 | 8/1988 | European Pat. Off. | 502/117 |
| 277004 | 8/1988 | European Pat. Off. | 502/117 |
| WO87/03887 | 7/1987 | PCT Int'l Appl. | 502/117 |

Primary Examiner—Patrick P. Garvin

Attorney, Agent, or Firm—Douglas N. Delime

[57] ABSTRACT

A monocyclopentadienyl or substituted monocyclopentadienyl metal complex containing compound useful as a polymerization catalyst corresponding to the formula:

$$CpMX_n^+A^-$$

wherein:

Cp is a single $\eta^5$-cyclopentadienyl or $\eta^5$-substituted cyclopentadienyl group optionally covalently bonded to M through a substituent;

M is a metal of Group 3-10 or the Lanthanide Series of the Periodic Table bound in the $\eta^5$ bonding mode to the cyclopentadienyl or substituted cyclopentadienyl group;

X each occurrence independently is selected from the group consisting of hydride, halo, alkyl, aryl, silyl, germyl, aryloxy, alkoxy, amide, siloxy, neutral Lewis base ligands and combinations thereof having up to 20 non-hydrogen atoms, and optionally one X together with Cp forms a metallocycle with M;

R is alkyl or aryl of up to 10 carbons;

n is one or two depending on the valence of M; and

A is a noncoordinating, compatible anion of a Bronsted acid salt.

10 Claims, No Drawings

METAL COMPLEX COMPOUNDS

CROSS-REFERENCE TO RELATED APPLICATION

This is a continuation-in-part of U.S. application Ser. No. 407,169, filed Sept. 14, 1989, now abandoned, the teachings of which are herein incorporated by reference.

BACKGROUND OF THE INVENTION

This invention relates to compositions of matter which are useful as catalysts, to a method for preparing these catalysts and to a method of using these catalysts. More particularly, this invention relates to catalyst compositions, to a method of preparing these catalyst compositions, to a method for polymerizing addition polymerizable monomers using the present catalysts.

In U.S. Ser. No. 8,800, filed Jan. 30, 1987 and now abandoned (published in equivalent form as EP 277,004) there are disclosed certain bis(cyclopentadienyl) metal compounds formed by reacting a bis(cyclopentadienyl) metal complex with salts of Bronsted acids containing a noncoordinating compatible anion. The reference discloses the fact that such complexes are usefully employed as catalysts in the polymerization of olefins. For the teachings contained therein the aforementioned U.S. Ser. No. 8,800 and EP 277,004 are herein incorporated in their entirety by reference thereto.

Despite the utility of the catalysts disclosed in the above prior art references it is desirable to produce even more efficient and useful catalysts for addition polymerizations. In particular the present investigations have led to certain improved metal complex containing compounds that are highly active as polymerization catalysts and desirably allow for the polymerization of a wide variety of monomers and mixtures of monomers.

SUMMARY OF THE INVENTION

According to the present invention there is now provided a monocyclopentadienyl or substituted monocyclopentadienyl metal complex containing compound useful as an olefin polymerization catalyst corresponding to the formula:

$$CpMX_n^+ A^-$$

wherein:
Cp is a single $\eta^5$-cyclopentadienyl or $\eta^5$-substituted cyclopentadienyl group optionally covalently bonded to M through a substituent;

M is a metal of Group 3-10 or the Lanthanide Series of the Periodic Table bound in an $\eta^5$ bonding mode to the cyclopentadienyl or substituted cyclopentadienyl group;

X each occurrence independently is selected from the group consisting of hydride, halo, alkyl, aryl, silyl, germyl, aryloxy, alkoxy, amide, siloxy, neutral Lewis base ligands and combinations thereof having up to 20 non-hydrogen atoms, and optionally one X together with Cp forms a metallocycle with M;

n is one or two depending on the valence of M; and

A is a noncoordinating, compatible anion of a Bronsted acid salt.

Such compounds are usefully employed in Ziegler-Natta type polymerization processes to prepare polymers for molding, film, sheet, extrusion foaming and other applications. The compounds may also be utilized in hydrogenation reactions, catalytic cracking and other industrial processes.

DETAILED DESCRIPTION OF THE INVENTION

The compounds of the present invention are prepared by combining:

a) at least one first component which is a mono(cyclopentadienyl) derivative of a metal of Group 3-10 or the Lanthanide Series of the Periodic Table of the Elements containing at least one substituent which will combine with the cation of a second component (described hereinafter) which first component is capable of forming a cation formally having a coordination number that is one less than its valence, b) and at least one second component which is a salt of a Bronsted acid and a noncoordinating, compatible anion.

More particularly the noncoordinating, compatible anion of the Bronsted acid salt may comprise a single coordination complex comprising a chargebearing metal or metalloid core, which anion is both bulky and non-nucleophilic. The recitation "metalloid", as used herein, includes non-metals such as boron, phosphorus and the like which exhibit semi-metallic characteristics.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

As used herein, the recitation "noncoordinating, compatible anion" means an anion which either does not coordinate to the monocyclopentadienyl or substituted monocyclopentadienyl group containing cation or which is only weakly coordinated to said cation thereby remaining sufficiently labile to be displaced by a neutral Lewis base. A noncoordinating, compatible anion specifically refers to a compatible anion which when functioning as a charge balancing anion in the catalyst system of this invention does not transfer an anionic substituent or fragment thereof to said cation thereby forming a neutral four coordinate metallocene and a neutral metal byproduct. "Compatible anions" are anions which are not degraded to neutrality when the initially formed complex decomposes and are noninterfering with desired subsequent polymerization or other uses of the complex.

Monocyclopentadienyl and substituted monocyclopentadienyl groups for use according to the present invention are more specifically depicted by the formula:

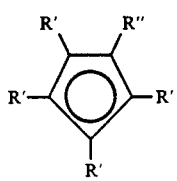

wherein:
R' each occurrence is independently selected from the group consisting of hydrogen, halogen, alkyl, aryl, haloalkyl, alkoxy, aryloxy, and silyl groups of up to 20 non-hydrogen atoms, or two or more R' groups together may form a fused ring system; and R" individually may be R' or a group that is covalently bonded to M of the formula: —Z—Y—, wherein Z is a divalent moiety comprising oxygen, boron, or a member of group 14 of the periodic table of the elements; and Y is a linking group covalently bonded to the metal comprising nitrogen, phosphorus, oxygen or sulfur, or optionally Z and Y together form a fused ring system.

In a highly preferred embodiment R" is

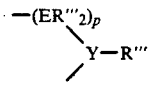

wherein:

E independently each occurrence is carbon, silicon, or germanium;

p is an integer from 1 to 4;

Y is nitrogen or phosphorous; and

R''' independently each occurrence is alkyl, aryl, silyl or combinations thereof having up to 10 carbon or silicon atoms.

Thus highly preferred compositions according to the invention correspond to the formula:

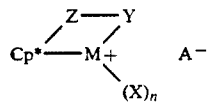

wherein:

M is zirconium or titanium;

Cp* is a cyclopentadienyl or substituted cyclopentadienyl group bound in an $\eta^5$ bonding mode to M;

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$; wherein:

R* each occurrence is independently selected from the group consisting of hydrogen, alkyl, aryl, silyl, halogenated alkyl, halogenated aryl groups having up to 20 non-hydrogen atoms, and mixtures thereof, or two or more R* groups from Y, Z, or both Y and Z form a fused ring system, Y is a nitrogen or phosphorus containing group corresponding to the formula —N(R'''')— or —P(R'''')—, wherein R'''' is $C_{1-10}$ alkyl or aryl, i.e. an amido or phosphido group;

X is independently each occurrence halo, alkyl, aryl, alkoxy, or aryloxy of up to 20 carbons;

n is one or two; and

A— is a noncoordinating, compatible anion of a Bronsted acid salt.

Illustrative, but not limiting examples of monocyclopentadienyl metal components (first components) which may be used in the preparation of the compounds of this invention are derivatives of titanium, zirconium, hafnium, chromium, lanthanum, etc. Preferred components are titanium or zirconium compounds. Examples of suitable monocyclopentadienyl metal compounds are hydrocarbyl-substituted monocyclopentadienyl metal compounds such as cyclopentadienylzirconium trimethyl, cyclopentadienylzirconium triethyl, cyclopentadienylzirconium tripropyl, cyclopentadienyltitanium trimethyl, cyclopentadienyltitanium triphenyl, cyclopentadienylscandium bis(p-tolyl), cyclopentadienylchromium 2,4-pentadienyl, pentamethylcyclopentadienylyitrium bis(bistrimethylsilylmethyl), pentamethylcyclopentadienylscandium bis(bistrimethylsilylmethyl), pentamethylcyclopentadienyllanthanum bis(bistrimethylsilylmethyl), etc.; hydrocarbyloxy substituted compounds such as cyclopentadienyltitanium triisopropoxide, cyclopentadienylzirconium triphenoxide, etc.; halo substituted compounds such as cyclopentadienylzirconium trichloride, indenyltitanium trichloride, pentamethylcyclopentadienylhafnium trichloride, cyclopentadienylyitrium dichloride, etc.; and compounds comprising mixtures of substituents such as cyclopentadienyltitanium isopropoxide dimethyl, pentamethylcyclopentadienylzirconium methyl dichloride, cyclopentadienyllanthanum chloro isopropoxide, (tert-butylamido)(tetramethyl-$\eta^5$-cyclopentadienyl)-1,2-ethanediylzirconium dichloride, (tert-butylamido)(tetramethyl-$\eta^5$-cyclopentadienyl)-1,2-ethanediyltitanium dichloride, (methylamido)(tetramethyl-$\eta^5$-cyclopentadienyl)-1,2-ethanediylzirconium dichloride, (methylamido)(tetramethyl-$\eta^5$-cyclopentadienyl)-1,2-ethanediyltitanium dichloride, (ethylamido)(tetramethyl-$\eta^5$-cyclopentadienyl)-methylenetitanium dichloro, (tertbutylamido)dibenzyl(tetramethyl-$\eta^5$-cyclopentadienyl)silanezirconium dibenzyl, (benzylamido)dimethyl(tetramethyl-$\eta^5$-cyclopentadienyl)silanetitanium dichloride, (phenylphosphido)dimethyl(tetramethyl-$\eta^5$-cyclopentadienyl)silanezirconium dibenzyl, and the like.

The last enumerated compounds of the above list is illustrative of compounds containing covalent bonds between the metal atom and substituents of the cyclopentadienyl ring. Preferred substituents are those which are capable of $\sigma$-bonding to the metal atom. Such components are readily prepared by combining the corresponding metal chloride with a dilithium salt of the substituted cyclopentadienyl group such as a cyclopentadienyl-alkanediyl, cyclopentadienyl—silane amide, or cyclopentadienyl—phosphide compound. The reaction is conducted in an inert liquid such as tetrahydrofuran, $C_{5-10}$ alkanes, toluene, etc. utilizing conventional synthetic procedures. Certain of these compounds are further disclosed and claimed in the recently filed U.S. patent application Ser. No. 401,344, filed Aug. 31, 1989, now abandoned, and assigned to the same assignee as the present invention, which teachings are incorporated herein in their entirety by reference thereto.

Compounds useful as a second component in the preparation of the compounds of this invention will comprise a cation, which is a Bronsted acid capable of donating a proton, and a compatible noncoordinating anion. Preferred anions are those containing a single coordination complex comprising a charge-bearing metal or metalloid core which anion is relatively large (bulky), capable of stabilizing the active catalyst species (the Group 3-10 or Lanthanide Series cation) which is formed when the two components are combined and said anion will be sufficiently labile to be displaced by olefinic, diolefinic and acetylenically unsaturated substrates or other neutral Lewis bases such as ethers, nitriles and the like. Suitable metals, then, include, but are not limited to, aluminum, gold, platinum and the like. Suitable metalloids include, but are not limited to, boron, phosphorus, silicon and the like. Compounds containing anions which comprise coordination complexes containing a single metal or metalloid atom are, of course, well known and many, particularly such compounds containing a single boron atom in the anion portion, are available commercially. In light of this, salts containing anions comprising a coordination complex containing a single boron atom are preferred.

Preferably the second component useful in the preparation of the catalysts of this invention may be represented by the following general formula:

$$(L-H)_d^+[A]^{d-}$$

wherein:
L is a neutral Lewis base;
(L—H)+ is a Bronsted acid; and
A is a compatible, noncoordinating anion.
More preferably $A^{d-}$ corresponds to the formula:

$$[M'^{m+}Q_n]^{d-}$$

wherein:
m is an integer from 1 to 7;
n is an integer from 2 to 8;
n-m=d;
M' is a metal or metalloid selected from Groups 5-15 of the Periodic Table of the Elements; and
Q independently each occurrence is selected from the Group consisting of hydride, dialkylamido, halide, alkoxide, aryloxide, hydrocarbyl, and substituted-hydrocarbyl radicals of up to 20 carbons with the proviso that in not more than one occurrence is Q halide.

Second components comprising boron which are particularly useful in the preparation of catalysts of this invention may be represented by the following general formula:

$$[L-H]^+[BQ_4]^-$$

wherein:
L is a neutral Lewis base;
[L—H]+ is a Bronsted acid;
B is boron in a valence state of 3; and
Q is as previously defined.

Illustrative, but not limiting, examples of boron compounds which may be used as a second component in the preparation of the improved catalysts of this invention are trialkyl-substituted ammonium salts such as triethylammonium tetraphenylborate, tripropylammonium tetraphenylborate, tri(n-butyl)ammonium tetraphenylborate, trimethylammonium tetra(p-tolylborate), tributylammonium tetrakis-pentafluorophenylborate, tripropylammonium tetrakis-2,4-dimethylphenylborate, tributylammonium tetrakis-3,5-dimethylphenylborate, triethylammonium tetrakis-(3,5-di-trifluoromethylphenyl)borate and the like. Also suitable are N,N-dialkyl anilinium salts such as N,N-dimethylanilinium tetraphenylborate, N,N-diethylanilinium tetraphenylborate, N,N-2,4,6-pentamethylanilinium tetraphenylborate and the like; dialkyl ammonium salts such as di-(i-propyl)ammonium tetrakispentafluorophenylborate, dicyclohexylammonium tetraphenylborate and the like; and triaryl phosphonium salts such as triphenylphosphonium tetraphenylborate, tri(methylphenyl)phosphonium tetrakis-pentafluorophenylborate, tri(dimethylphenyl)phosphonium tetraphenylborate and the like.

Similar lists of suitable compounds containing other metals and metalloids which are useful as second components could be made, but such lists are not deemed necessary to a complete disclosure. In this regard, it should be noted that the foregoing lists is not intended to be exhaustive and other boron compounds that would be useful as well as useful components containing other metals or metalloids would be readily apparent from the foregoing general formula and examples to those skilled in the art.

In general, and while most first components identified above may be combined with most second components identified above to produce an active olefin polymerization catalyst, it is important to continued polymerization operations that either the metal cation initially formed from the first component or a decomposition product thereof be a relatively stable catalyst. It is also important that the anion of the second compound be stable to hydrolysis when an ammonium salt is used. Further, it is important that the acidity of the second component be sufficient, relative to the first, to facilitate the needed proton transfer. Conversely, the basicity of the metal complex must also be sufficient to facilitate the needed proton transfer. Certain metallocene compounds are resistant to reaction with all but the strongest Bronsted acids and thus are not suitable as first components to form the catalysts of this invention with all second components. Most preferred monocyclopentadienyl metal compounds are those which can be hydrolyzed by aqueous solutions.

With respect to the combination of first (metal containing) component to second component to form a catalyst of this invention, it should be noted that the two components that are combined for preparation of the active catalyst must be selected so as to avoid transfer of a fragment of the anion, particularly an aryl group, or a fluorine or hydrogen atom to the metal cation, thereby forming a catalytically inactive species. This could be done by steric hinderance, resulting from substitutions on the cyclopentadienyl carbon atoms as well as substitutions on the aromatic carbon atoms of the anion. It follows, then, that first components comprising perhydrocarbyl-substituted cyclopentadienyl radicals could be effectively used with a broader range of second compounds than could first components comprising unsubstituted cyclopentadienyl radicals. As the amount and size of the substitutions on the cyclopentadienyl radicals are reduced, however, more effective catalysts are obtained with second compounds containing anions which are more resistant to degradation, such as those with substituents on the ortho positions of the phenyl rings. Another means of rendering the anion more resistant to degradation is afforded by fluorine substitution, especially perfluoro-substitution, in the anion. Fluoro-substituted stabilizing anions may, then, be used with a broader range of first components.

In general, the catalyst can be prepared by combining the two components in a suitable solvent at a temperature within the range from about $-100°$ C. to about $300°$ C. The catalyst may be used to polymerize $\alpha$-olefins and/or acetylenically unsaturated monomers having from 2 to about 18 carbon atoms and/or diolefins having from 4 to about 18 carbon atoms either alone or in combination. The catalyst may also be used to polymerize $\alpha$-olefins, diolefins an/or acetylenically unsaturated monomers in combination with other unsaturated monomers. In a preferred embodiment the catalysts are employed to prepare copolymers of mixtures of vinyl aromatic monomers with olefins other than a vinyl aromatic monomer, specifically copolymers of styrene with ethylene or propylene. In general, the polymerization may be accomplished at conditions well known in the prior art. It will, of course, be appreciated that the catalyst system will form in situ if the components thereof are added directly to the polymerization process and a suitable solvent or diluent, including condensed monomer, is used in said polymerization process. It is, however, preferred to form the catalyst in a separate step in a suitable solvent prior to adding the same to the polymerization step. While the catalysts may not contain pyrophoric species, the catalysts' components are sensitive to both moisture and oxygen and should be handled and transferred in an inert atmosphere such as nitrogen, argon or helium.

As indicated supra, the improved catalyst of the present invention will, preferably, be prepared in a suitable solvent or diluent. Suitable solvents or diluents include any of the solvents known in the prior art to be useful as solvents in the polymerization of olefins, diolefins and acetylenically unsaturated monomers. Suitable solvents, then, include, but are not necessarily limited to, straight and branched-chain hydrocarbons such as isobutane, butane, pentane, hexane, heptane, octane and the like; cyclic and alicyclic hydrocarbons such cyclohexane, cycloheptane, methylcyclohexane, methylcycloheptane and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexane, 3-methyl-1-pentene, 4-methyl-1-pentene, 1,4-hexadiene, 1-octene, 1-decene, styrene, and the like.

While the inventors do not wish to be bound by any particular theory, it is believed that when the two components used to prepare the improved catalysts of the present invention are combined in a suitable solvent or diluent, all or part of the cation of the second component (the acidic proton) combines with one of the substituents (X) on the first component. As a result a neutral compound, XH is liberated, which neutral compound either remains in solution or is liberated as a gas. In this regard, it should be noted that if X in the first component is hydride, hydrogen gas may be liberated. Similarly, if X is a methyl radical, methane may be liberated as a gas. If X is alkoxide an alcohol results, etc.

While still not wishing to be bound by any particular theory, it is also believed that as one of the first component substituents is liberated, the noncoordinating anion originally contained in the second component used in the catalyst preparation balances the charge of either the metal cation formed from the first component, or a decomposition product thereof. The metal cation and noncoordinating anion will remain so combined until the catalyst is contacted with one or more olefins, diolefins and/or acetylenically unsaturated monomers either alone or in combination with one or more other monomers or another neutral Lewis base. As indicated supra, the anion contained in the second compound must be sufficiently labile to permit rapid displacement by an monomer to facilitate polymerization.

The chemical reactions which occur in forming the catalysts of this invention may, when a preferred, boron containing compound is used as the second component, be represented by reference to the general formula set forth herein as follows:

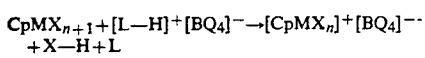

wherein Cp, M, X, n and Q have the previously identified meanings.

In general the stability and rate of formation of the products in the foregoing reaction equations, particularly the metal cation, will vary depending upon the choice of the solvent, the acidity of the $[L—H]^+$ selected, the particular L, the anion, the temperature at which the reaction is completed and the particular monocyclopentadienyl derivative of the metal selected. Generally, the initially formed ion-pair will be an active polymerization catalyst and will polymerize $\alpha$-olefins, diolefins and acetylenically unsaturated monomers either alone or in combination with other monomers. In some cases, however, the initial metal cation will decompose to yield an active polymerization catalyst.

As indicated supra, most first compounds identified above will combine with most second compounds identified above to produce an active catalyst, particularly an active polymerization catalyst. The actual active catalyst species is not, however, always sufficiently stable as to permit its separation and subsequent identification. Moreover, and while many of the initial metal cations formed are relatively stable, it has become apparent that the initially formed metal cation frequently decomposes into one or more other catalytically active species.

In general, catalysts according to the present invention can be selected so as to produce polymer products that will be free of certain trace metals generally found in polymers produced with Ziegler-Natta type catalysts containing cocatalysts such as aluminum or magnesium based compounds. The polymer products produced with the catalyst of this invention should, then, have a broader range of applications than polymers produced with more conventional Ziegler-Natta type catalysts comprising a metal alkyl, such as an aluminum alkyl, or an aluminoxane. The catalysts may be employed as homogeneous catalysts or supported on the surface of a suitable support such as alumina or silica.

In a most preferred embodiment of the present invention Cp is pentamethylcyclopentadiene, M is titanium or zirconium, n is two, X is $C_{1-4}$ alkyl or alkoxide, and A is tetrakis-pentafluorophenyl borate.

In a further preferred embodiment, the catalyst is used to polymerize a lower $\alpha$-olefin, particularly ethylene or propylene, most preferably ethylene, at a temperature within the range from 0° C. to 200° C., preferably 25° C. to 100° C. and at a pressure within the range from atmospheric to 6,894 kPa (1000 psig) preferably 100 kPa to 3,400 kPa (15 to 500 psig). In a most preferred embodiment of the present invention, the catalyst will be used either to homopolymerize ethylene or to copolymerize ethylene with a lower $\alpha$-olefin having from 3 to 8 carbon atoms (including styrene) thereby yielding a plastic or an elastomeric copolymer. In both the preferred and most preferred embodiments, the monomers will be maintained at polymerization conditions for a nominal holding time within the range from about 1 to about 60 minutes and the catalyst will be used at a concentration within the range from about $10^{-7}$ to about $10^{-1}$ moles per mole of monomer.

Having thus broadly described the present invention it is believed that the same will become even more apparent by reference to the following examples. It will be appreciated, however, that the examples are presented solely for the purpose of illustration and should not be construed as limiting the invention.

EXAMPLE 1

In a drybox, at room temperature, 33 mg of pentamethylcyclopentadienyltitaniumisopropoxide dimethyl (CpTi(O-i-Pr)Me$_2$) (0.12 mmoles) was combined with 1 mL of benzene and the resultant solution was pipetted into a 250 mL 3-necked flask. A stopper, an adapter for the vacuum line, and a solid addition funnel were attached. The addition funnel was charged with 80 mg (0.10 mmoles) of triethylammonium tetrakis-pentafluorophenylborate ([HNEt$_3$]$^+$[B(C$_6$F$_5$)$_4$]$^-$). The addition funnel was stoppered and the apparatus was attached to a vacuum line. The benzene was removed from the flask under vacuum, and 75 mL of fresh benzene was distilled into the flask at $-78°$ C. under vacuum. After warming to room temperature, the solution was blanketed with 1 atmosphere of ethylene. The solid ([HNEt$_3$]$^+$[B(C$_6$F$_5$)$_4$]$^-$ was added at room temperature and the solution was observed to turn yellow. After 20 minutes the solution was black and a precipitate of polyethylene was observed. After one hour, the polymer was precipitated with methanol, collected, washed with methanol and dried in a vacuum oven overnight to yield 0.49 g of polymer.

EXAMPLE 2

The reaction conditions of Example 1 were substantially repeated utilizing pentamethylcyclopentadienyl titanium trimethyl and triethylammonium tetrakis-pentafluorophenyl borate. The reaction was conducted in toluene at room temperature for ~10 hrs. Methane gas and ammonia byproducts were observed. After heating to ~45° C. for one hour the toluene solvent was removed under vacuum leaving a black solid. The solid was washed three times with petroleum ether and dried under reduced pressure. The recovered product was identified as the desired pentamethylcyclopentadienyltitanium dimethyl tetrakis-pentafluorophenyl borate which may be employed to polymerize an olefin monomer under known Ziegler-Natta polymerization conditions.

What is claimed is:

1. A monocyclopentadienyl or substituted monocyclopentadienyl metal complex containing compound useful as an olefin polymerization catalyst corresponding to the formula:

$$CpMX_n{}^+A^-$$

wherein:

Cp is a single $\eta^5$-cyclopentadienyl or $\eta^5$-hydrocarbyl substituted cyclopentadienyl group optionally covalently bonded to M through a substituent;

M is a metal of Groups 3–10 or the Lanthanide Series of the Periodic Table bound in an $\eta^5$ bonding mode to the cyclopentadienyl or substituted cyclopentadienyl group;

X each occurrence independently is selected from the group consisting of hydride, halo, alkyl, aryl, silyl, germyl, aryloxy, alkoxy, amide, siloxy, neutral Lewis base ligands and combinations thereof having up to 20 non-hydrogen atoms, and optionally one X together with Cp forms a metallocycle with M;

n is one or two depending on the valence of M; and

A$^-$is a noncoordinating, compatible anion of a Bronsted acid salt.

2. The compound according to claim 1 wherein M is titanium or zirconium.

3. The compound according to claim 1 corresponding to the formula:

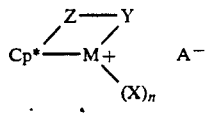

wherein:

M is zirconium or titanium;

Cp* is a cyclopentadienyl or hydrocarbyl substituted cyclopentadienyl group bound in an $\eta^5$ bonding mode to M;

Z is SiR*$_2$, CR*$_2$, SiR*$_2$SiR*$_2$, CR*$_2$CR*$_2$, CR*=CR*, CR*$_2$SiR*$_2$, or GeR*$_2$; wherein:

R* each occurrence is independently selected from the group consisting of hydrogen, alkyl, aryl, silyl, halogenated alkyl, halogenated aryl groups having up to 20 non-hydrogen atoms, and mixtures thereof, or two or more R* groups from Y, Z, or both Y and Z form a fused ring system, Y is a nitrogen or phosphorus containing group corresponding to the formula —N(R"")— or —P(R"'')—, wherein R"" is C$_{1-10}$ alkyl or aryl;

X is independently each occurrence halo, alkyl, aryl, alkoxy, or aryloxy of up to 20 carbons;

n is one or two; and

A$^-$ is a noncoordinating, compatible anion of a Bronsted acid salt.

4. The compound according to claim 1 wherein X is C$_{1-4}$ alkyl or alkoxy.

5. The compound according to claim 1 wherein n is 2.

6. The compound according to claim 1 wherein A is tetrakis-pentafluorophenyl borate.

7. A process for preparing a monocyclopentadienyl or substituted monocyclopentadienyl metal complex containing compound useful as an olefin polymerization catalyst corresponding to the formula:

$$CpMX_n{}^+A^-$$

wherein:

Cp is a single $\eta^5$-cyclopentadienyl or $\eta^5$-hydrocarbyl substituted cyclopentadienyl group optionally covalently bonded to M through a substituent;

M is a metal of Group 3–10 or the Lanthanide Series of the Periodic Table bound in an $\eta^5$ bonding mode to the cyclopentadienyl or substituted cyclopentadienyl group;

X each occurrence independently is selected from the group consisting of hydride, halo, alkyl, aryl, silyl, germyl, aryloxy, alkoxy, amide, siloxy, neutral Lewis base ligands and combinations thereof having up to 20 non-hydrogen atoms, and optionally one X together with Cp forms a metallocycle with M;

n is one or two depending on the valence of M; and

A is a noncoordinating, compatible anion of a Bronsted acid salt, the steps of the process comprising:

a) contacting a first component corresponding to the formula CpMX$_{n+1}$ wherein Cp, M, X and n are as above defined with a second component corresponding to the formula [L—H]$^+$[A]$^-$ wherein L is a neutral Lewis base and A is as previously defined, and b) recovering the resulting product.

8. A process according to claim 7 wherein the second component corresponds to the formula [L—H]+[BQ$_4$]− wherein L is a neutral Lewis base and Q independently each occurrence is selected from the groups consisting of hydride, dialkylamido, halide, hydrocarbyl, substituted hydrocarbyl and organometalloid of up to 20 carbons, with the proviso that in not more than one occurrence is Q halide.

9. A process according to claim 8 wherein Q is pentafluorophenyl.

10. A process according to claim 7 wherein the first component is a pentamethylcyclopentadienyl titanium dialkoxide or a pentamethylcyclopentadienyl titanium dialkyl having from 1 to 4 carbons on the alkoxide or alkyl group and the second component is a trialkylammonium tetrakis-pentafluorophenyl borate.

* * * * *

Adverse Decision In Interference

Patent No. 5,064,802, James C. Stevens, David R. Neithamer, METAL COMPLEX COMPOUNDS, Interference No. 103,112, final judgment adverse to the patentees rendered September 29, 2001, as to claims 1-10.

*(Official Gazette December 18, 2001)*